United States Patent
Hudak et al.

(10) Patent No.: US 7,282,181 B2
(45) Date of Patent: Oct. 16, 2007

(54) FLUID COLLECTION AND TESTING DEVICE

(75) Inventors: Andrew T. Hudak, Long Beach, CA (US); David M. Tierney, Newport Beach, CA (US); Daniel D. Wang, San Diego, CA (US); Robert L. Grenz, Santa Ana, CA (US); Roger R. Rohrdanz, Huntington Beach, CA (US); Kelly C. Alejandro, Anaheim, CA (US); Robert K. Galloway, Raleigh, NC (US)

(73) Assignee: Varian Inc., Palo Alto, CA (US)

( * ) Notice: Subject to any disclaimer, the term of this patent is extended or adjusted under 35 U.S.C. 154(b) by 242 days.

(21) Appl. No.: 10/942,493

(22) Filed: Sep. 16, 2004

(65) Prior Publication Data

US 2006/0057027 A1    Mar. 16, 2006

(51) Int. Cl.
- *B01L 3/00* (2006.01)
- *B01L 11/00* (2006.01)
- *G01N 1/12* (2006.01)
- *B65D 81/00* (2006.01)

(52) U.S. Cl. .................. 422/99; 73/864.72; 422/101; 600/573

(58) Field of Classification Search ............ 73/864.72; 422/99, 101; 600/573
See application file for complete search history.

(56) References Cited

U.S. PATENT DOCUMENTS

| | | | | |
|---|---|---|---|---|
| 4,014,322 A | * | 3/1977 | Shah | 600/573 |
| 5,393,496 A | * | 2/1995 | Seymour | 422/101 |
| 6,372,513 B1 | | 4/2002 | Nguyen et al. | |
| 6,464,939 B1 | | 10/2002 | Bachand et al. | |
| 6,468,474 B2 | | 10/2002 | Bachand et al. | |
| 6,489,172 B1 | | 12/2002 | Bachand et al. | |
| 7,114,403 B2 | * | 10/2006 | Wu et al. | 73/864.72 |

FOREIGN PATENT DOCUMENTS

| | | |
|---|---|---|
| EP | 0 250 170 A2 | 12/1987 |
| EP | 0 520 408 A2 | 6/1992 |

OTHER PUBLICATIONS

ACON product insert literature entitled "Oral Fludi Drug Screen Device", distributed by ACON Laboratories, Inc., San Diego, CA effective Dec. 30, 2003.

\* cited by examiner

*Primary Examiner*—Jill Warden
*Assistant Examiner*—Lore Ramillano
(74) *Attorney, Agent, or Firm*—Walter Hackler; Bella Fishman

(57) ABSTRACT

A fluid collection and testing device includes a collection vial having a bottom and an open top along with an expresser sized for insertion into the vial open end. The expresser includes a ribbed base enabling fluid to pass therethrough and a support member holds the expresser within the collection vial with the ribbed base in a spaced apart relationship with the vial bottom. A fluid collector includes an absorbent member capturing a fluid and the absorbent member is sized for insertion into the expresser and is compressible against the ribbed base for releasing captured fluid through the ribbed base and into the vial bottom. A catch mechanism is provided for latching the fluid collector to the expresser after insertion into the expresser for enabling simultaneous removal of the expresser and the fluid collector from the collection vial.

19 Claims, 3 Drawing Sheets

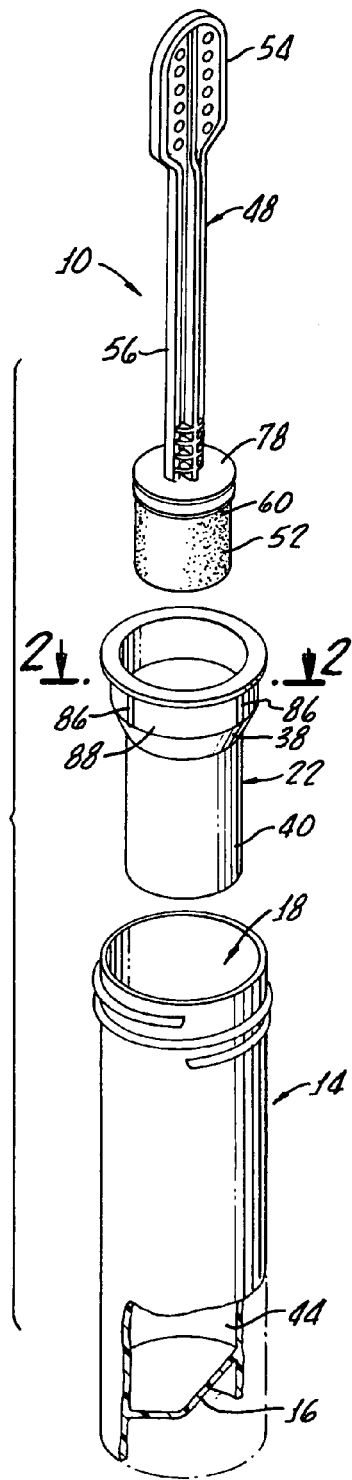
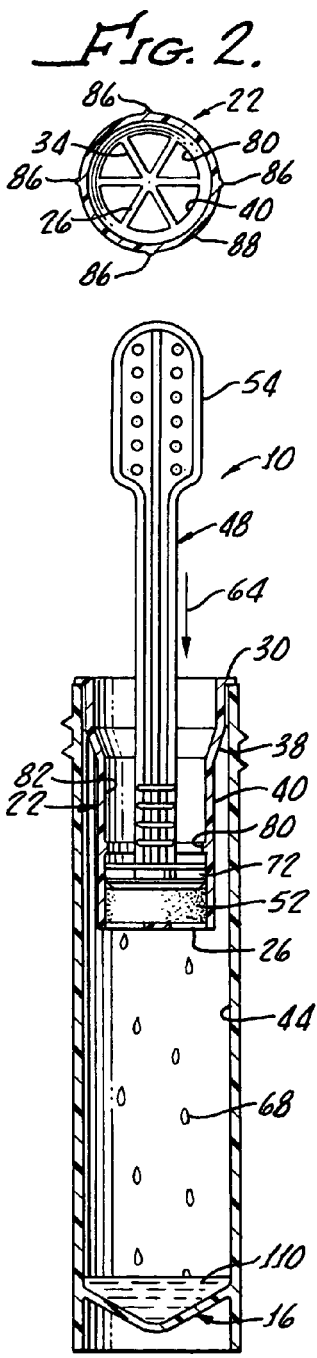
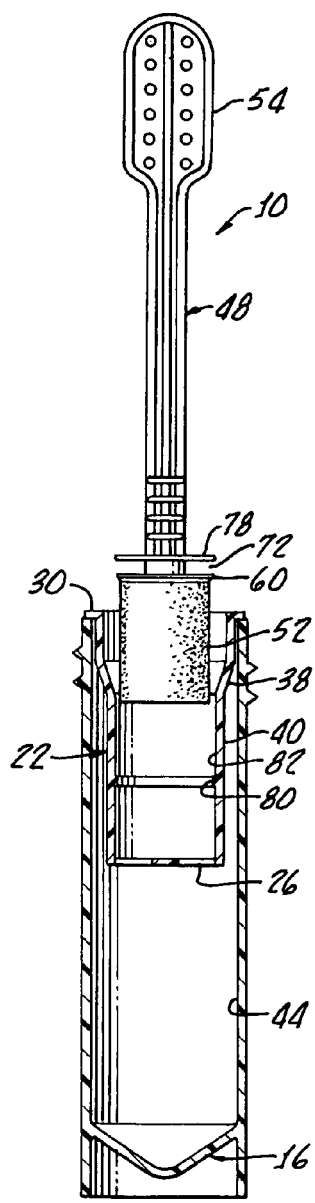
FIG. 1.
FIG. 2.
FIG. 3.
FIG. 4.

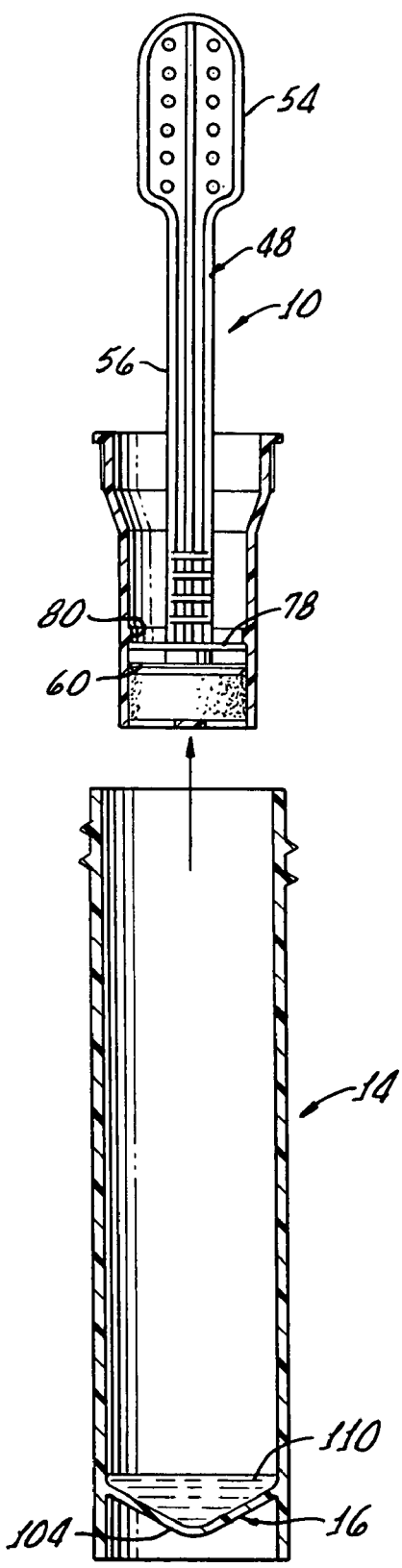
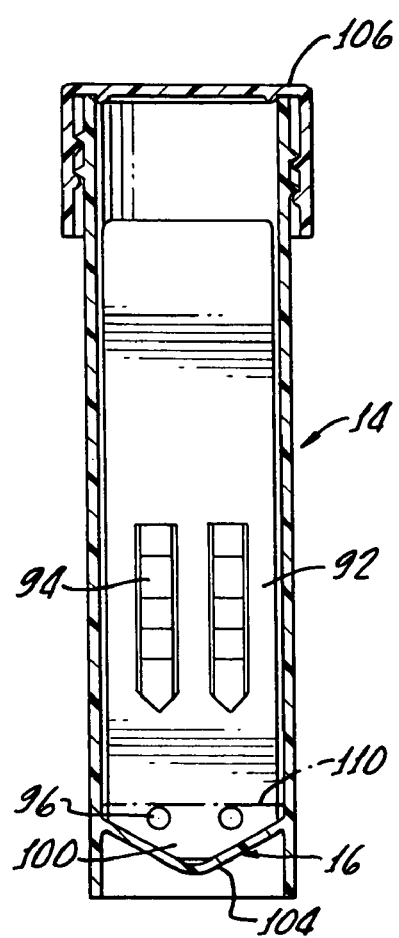
*FIG. 5.*  *FIG. 6.*

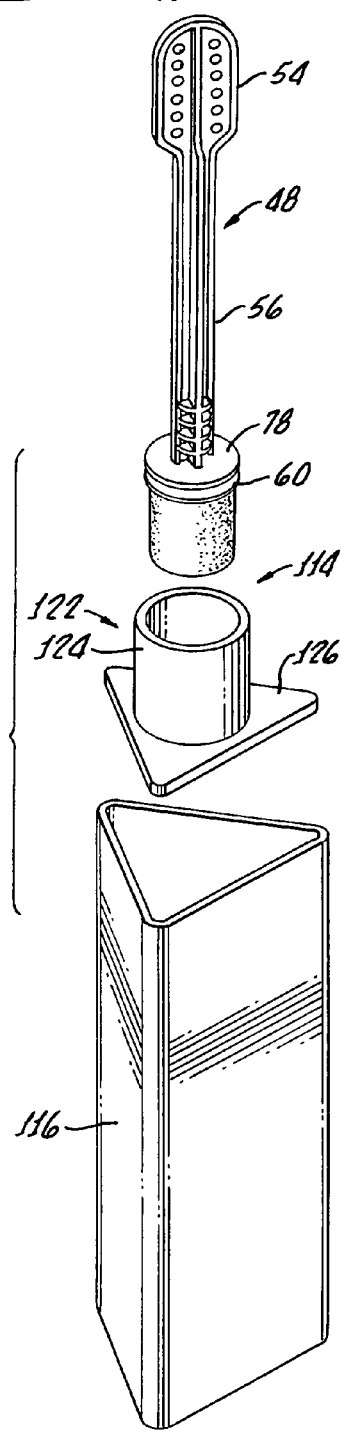
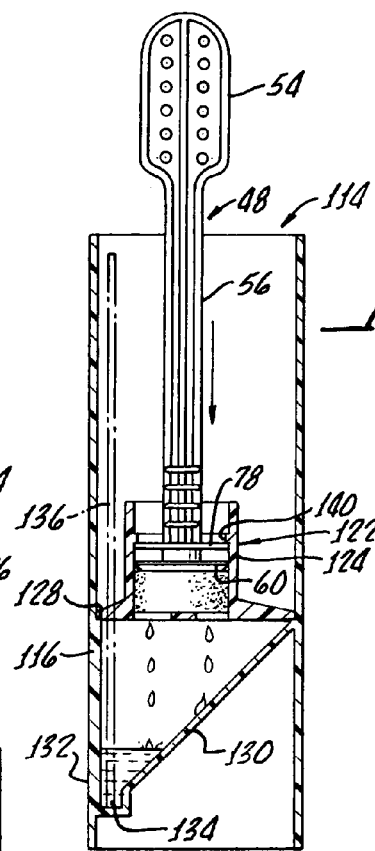
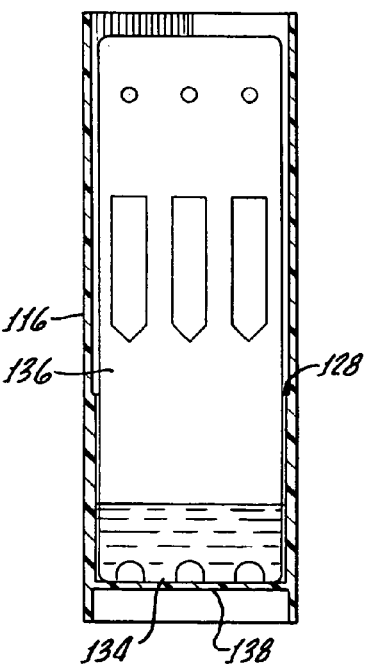

FLUID COLLECTION AND TESTING DEVICE

FIELD OF THE INVENTION

The present invention generally relates to fluid specimen collection and testing devices and is more specifically directed to an oral fluid or saliva collection and testing devices.

BACKGROUND OF THE INVENTION

Sampling and testing of body fluids is common for both testing and monitoring the human body for any number of biochemical or physiological conditions and, of course, for determining the general state of health of an individual.

Use of saliva as a testing medium is often preferable due to its availability without intrusive methods such as is required in sampling of blood. Urine samples, although non invasive, require patient monitoring during sampling to insure integrity. Accordingly, the use of saliva as a medium in biochemical and physiological analysis is desirable since it can be obtained by non-invasive methods and is easily monitored.

In addition, saliva has been found to be a very reliable carrier of analyte indicators and lateral flow chromatographic immunoassays which are useful for the qualitative detection of amphetamines, methamphetamine, cocaine, opiates, THC and their metabolites and other drugs of misuse and substances along with applications including nucleic acid markers and viral infections such as HIV.

Although saliva may be advantageously used in the analysis of a patient's biochemistry, problems still remain in the collection of saliva and in the handling thereof by laboratory technicians. As in the testing of any body fluid, minimum exposure due to handling is of utmost importance.

The present invention is directed to a fluid collection and testing device which facilitates a separation of saliva from a collector and enables drip-free and easy isolation of the saliva specimen in a container.

SUMMARY OF THE INVENTION

A fluid collection and testing device in accordance with the present invention generally includes a collection vial having a bottom and an open top. An expresser is provided and sized for insertion into the vial open end with the expresser having a ribbed base for enabling fluid to pass therethrough. A support member is provided for holding the expresser within the collector vial with the ribbed base in a spaced apart relationship with the vial bottom. In this manner, separate fluid, such as saliva, is collected in the vial, which is isolated from the expresser after separation from a fluid collector.

In that regard, a fluid collector in accordance with the present invention includes an absorbent member for capturing a fluid with the absorbent member being sized for insertion into the expresser and compressible against the ribbed base for releasing captured fluid therein through the ribbed base and into the vial bottom.

A catch mechanism is provided for latching the fluid collector to the expresser after insertion into the expresser and this enables the removal of the expresser from the collection vial with the fluid collector. This significantly reduces the possibility of contact or exposure of the saliva after expressing.

More particularly, a fluid test card may be provided and sized for insertion into the collection vial and includes test strips for wicking fluid from the vial bottom.

In one embodiment of the present invention, the collection vial is cylindrical and the vial bottom has a conical shape for accumulation of fluid and centering of the test card therein. To facilitate such centering and to insure contact of the test card with the fluid in the bottom of the collection vial, the test card may include a bottom, which is shaped for conforming to and nesting in the conical shape of the collection vial bottom.

In an alternative embodiment in accordance with the present invention, the collection vial may be a triangular tube and the vial bottom may be slanted toward a side of the tube and include a trough for accumulation of fluid and receiving a test card bottom.

Still more particularly, the device in accordance with the present invention may include crush ribs disposed on a circumference of the expresser for providing an interference fit with an inside circumference of the collection vial. This structure is provided to both stabilize the expresser within the collection vial and to prevent premature removal of the expresser from the collection vial.

The support member hereinabove noted may include an outwardly extending flange for engaging the vial top in order to suspend the expresser within the collection vial with the ribbed base in a spaced apart relationship with the vial bottom, as hereinabove noted.

In further summary of the present invention, the fluid collector includes a handle and a stem interconnecting the absorbent member and the handle and the catch mechanism includes a skirt radially extending from the stem and a ring disposed on inner circumference of the expresser for latching the skirt. In operation, the skirt is pushed past the ring during expressing of saliva from the absorbent member and withdrawal of the fluid collector, now latched, or attached, to the expresser, removes the expresser simultaneously therewith from the collection vial.

The fluid collector further includes a second skirt adjacent the absorbent member causing compression of the absorbent member against the ribbed base upon movement of the inserted fluid collector toward the vial bottom.

In addition, the absorbent member is sized for enabling expansion, after compression, in order to both force the skirt against the ring to provide a positive latch and to cause absorption of any surface fluid on the absorbent member caused by compression. This eliminates dripping of fluid during withdrawal of the collection and expresser from the vial.

In order to facilitate the insertion of the expresser into the collection vial, the expresser may be provided with a tapered sidewall portion.

A method in accordance with the present invention for a collection of fluid generally includes providing a collection vial and inserting an expresser thereinto. The method further includes capturing a fluid in an absorbent member attached to a fluid collector and inserting the absorbent member into the expresser with the fluid collector.

The absorbent member is compressed within the expresser to release captured fluid into the vial. The method further includes latching the fluid collector to the expresser and thereafter removing the latched fluid collector and expresser from the vial without dripping. A test card may thereafter be inserted into the vial for performing analysis in the fluid and the vial may be capped for storage of the fluid or for subsequent testing or disposal.

BRIEF DESCRIPTION OF THE DRAWINGS

The advantages and features of the present invention will be better understood by the following description when considered in conjunction with the accompanying drawings in which:

FIG. 1 is an exploded perspective view of a fluid collection and testing device in accordance with the present invention generally showing a collection vial, an expresser along with a fluid collector including an absorbent member for capturing a fluid;

FIG. 2 is a cross section view of the expresser shown in FIG. 1 and taken along the line 2-2 and showing a ribbed base;

FIG. 3 is a cross sectional view of the device shown in FIG. 1 showing the expresser inserted into the collection vial and supported therein with the ribbed base in a spaced apart relationship with a vial bottom along with the absorbent member being introduced into the expresser by the fluid collector;

FIG. 4 is another cross sectional view illustrating full insertion of the absorbent member into the expresser and compression thereof by the fluid collector against the expresser ribbed base and latching of the fluid collector to the expresser as will be hereinafter described in greater detail;

FIG. 5 is still another cross sectional view illustrating the simultaneous removal of the fluid collector and expresser from the vial;

FIG. 6 shows a fluid test card inserted into the collection vial with test strips for wicking fluid from the vial bottom along with a cap fitted to an open top of the collection vial;

FIG. 7 is an alternative embodiment of the present invention generally illustrating a triangular fluid collection vial along with an expresser and a fluid collector with an absorbent member;

FIG. 8 is a cross sectional view of the embodiment shown in FIG. 7 illustrating compression of the absorbent member and latching of the fluid collector to the expresser; and FIG. 9 is a cross sectional view illustrating a fluid test card inserted into the collection vial with test strips for wicking fluid from the vial bottom.

DETAILED DESCRIPTION OF THE INVENTION

With reference to FIG. 1, there is shown a fluid collection and testing device 10 in accordance with the present invention generally including a cylindrical collection vial 14 having a bottom 16 and an open top 18 along with an expresser 22 sized for insertion into the vial open top 18, as illustrated in FIGS. 3-4.

As more clearly shown in FIG. 2, the expresser 22 includes a ribbed base 26 for enabling fluid to pass therethrough and a support member, such as a flange 30, outwardly extending for engaging the vial top 18, as illustrated in FIGS. 3-4.

It should be appreciated that the vial 14 and expresser 22 as well as all of other components of the present invention may be formed from conventional suitable materials such as plastics and the like.

As shown in FIG. 2, the ribbed base 26 may include a plurality of radial ribs 34, although other rib patterns may be suitable for enabling passage of fluid therethrough.

As shown in FIGS. 3-4, the support member, or flange, 30 holds the expresser 22 within the collection vial 14 with the ribbed base 26 in a spaced apart relationship with the vial bottom 16. Other support members, not shown, may be utilized in accordance with the present invention.

As illustrated in FIG. 1, the expresser 22 may include a tapered sidewall portion 38 for facilitating insertion of the expresser 22 into the collection vial 14. As shown in FIGS. 3-4, a narrowed portion 40 of the expresser 22 is disposed in a spaced apart relationship with an inner circumference 44 of the collection vial 14.

In accordance with the present invention, a fluid collector 48 including an absorbent member 52, handle 54, and inner connecting stem 56 is provided for accumulating a sample from a patient's mouth, not shown.

The absorbent member 52, which may be a foam or sponge-like material, is sized for insertion into the expresser 22, see FIGS. 3-4, and compressible against the ribbed base 26, see FIG. 4, for releasing captured fluid through the ribbed base 26 and into the vial bottom 16.

Compression of the absorbent member 52 is facilitated by a skirt 60 extending radially from the stem 56. When the collector 48 is pushed toward the vial bottom 16, as indicated by the arrow 64 in FIG. 4, member 52 compresses and releases, or expresses captured fluid 68, as also shown in FIG. 4.

As illustrated in FIGS. 3-4, a catch mechanism 72 is provided for latching the fluid collector 48 to the expresser 22 after insertion of the fluid collector 48 into the expresser 22. This latching enables the removal of the expresser from the collection vial 14 simultaneously with the fluid collector 48 and thus subsequent touching or handling of the expresser 22 now exposed to saliva is not necessary.

As an example, the catch mechanism 72 may include in combination, a skirt 78 radially extending from the collector stem 56 and a ring 80 disposed on an inner circumference 82 of the expresser 22, see also FIG. 2. The skirt 78 has a diameter greater than a diameter of the expresser measured within the ring 80 and accordingly once the skirt 78 is forced passed the ring 80 during compression of the absorbent member 52 (see FIG. 4), removal of the collector 48 from the vial 14 lifts the expresser 22 simultaneously with the collector 48 from the vial 14, as shown in FIG. 5.

As hereinabove noted, the absorbent member 52 is sized, i.e. has a length, for permitting expansion subsequent to compression. This subsequent expansion forces the skirt 78 against the ring 80 while at the same time reabsorbs any fluid forced to a surface 52A of the member 52 during compression. This reabsorption eliminates, or significantly reduces, the possibility of fluid dripping during withdrawal of the collector 48 and expresser 22 from the vial 14. This, of course, reduces the possibility of contaminating adjacent surfaces (not shown).

In order to stabilize the expresser 22 within the vial 14 and also prevent premature removal of the expresser 22 from the vial 14, crush ribs 86 may be provided on a circumference 88 of the expresser 22 for providing an interference fit with the inner circumference 44 of the collection vial 14, see FIGS. 1 and 2.

Following the expressing of fluid into the collection vial 14 and removal of the collector 48 and the expresser 22, a fluid test card 92 may be inserted into the collection vial 14, see FIG. 6. The card 92 may be a conventional lateral flow chromatographic immunoassay device having test strips 94 with bottom inlets 96 for wicking fluid from the vial bottom 16.

As shown in FIG. 6, a card bottom 100 may have a generally arcuate, or triangular shape 102 for conforming to the vial bottom 16 which has a conical shape 104 for accumulation of fluid 110 and centering of the test card 92, as illustrated in FIG. 6.

Operation of the device 10 is illustrated in FIGS. 3-6. The expresser 22 is first inserted into the vial 14 with the crush ribs 86 providing a snug fit therein.

Thereafter the collector 48, subsequent to swabbing the inside of a mouth and tongue (not shown) to collect oral fluid, is inserted into the expresser 22 (FIG. 3). Downward pressure on the absorbent member 52 via the handle 54 and stem 56 as indicated by the arrow 64 causes the second skirt 60 to compress the absorbent member against the ribbed base thus releasing captured fluid 68 (FIG. 4).

Subsequently, as hereinabove described, the collector 48 and expresser 22 are simultaneously removed from the vial 14 due to latching between the collector 48 and expresser 22 by the catch mechanism 72 which includes the skirt 78 and ring 80. Expansion of the absorbent member 52 after compression, as hereinabove noted, prevents dripping of fluid.

The test card 92 may then be inserted into the vial 14 for sufficient period of time to wick fluid 110 from the bottom 16 of the vial 14. After wicking, the card 92 may be removed from the vial or left in the vial 14 which may be sealed with a cap 106 in a conventional manner for preserving remaining fluid 110 in the vial bottom 16 for subsequent testing or disposal (FIG. 6).

With reference now to FIGS. 7-9, there is shown an alternative embodiment device 114 in accordance with the present invention, common reference characters denoting identical or substantially similar components to those described in connection with the device 10, hereinabove described and illustrated in FIGS. 1-6.

In this embodiment 114, a collection vial 116 comprises a triangular tube as best shown in FIG. 7. An expresser 122 includes a circular chimney 124 with a triangular flange 126 for engaging a vial wall step 128.

In the embodiment 114, the vial 116 includes a vial bottom 130 slanted toward a side 132 of the vial 116 and includes a trough 134 for accumulation of fluid and receiving a test card 136. The test card 136 is similar to the card 92 except, as shown in FIG. 6, includes a flat bottom 130 for nesting in the trough 134.

As hereinabove discussed in connection with the embodiment 10, the flange 78 engages a ring 140 for latching the collector 48 to the expresser 122 to enable simultaneous removal from the vial.

Although there has been hereinabove described a specific saliva testing/expresser/collection device in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements, which may occur to those skilled in the art, should be considered to be within the scope of the present invention as defined in the appended claims.

What is claimed is:

1. A fluid collection and testing device comprising:
a cylindrical collection vial having a bottom and an open top;
a fluid test card, insertable into said cylindrical collection vial and including vial bottom wicking fluid test strips;
an expresser, which inserts into the vial open top, said expresser having a ribbed base, which passes fluid therethrough and a support member holding said expresser within said cylindrical collection vial with said ribbed base in a spaced apart relationship with the vial bottom, said vial bottom having a conical shape accumulating fluid and containing the fluid test card therein;
a fluid collector including an absorbent member capturing a fluid, said absorbent member being inserted into said expresser and compressible against said ribbed base releasing captured fluid through said ribbed base and into the cylindrical collection vial bottom; and
a catch mechanism latching said fluid collector to said expresser after insertion of the absorbing member into said expresser and enabling expansion of said absorbent member, after compression, to prevent dripping of fluid upon withdrawal of the fluid collector and expresser from the cylindrical collection vial.

2. The device according to claim 1, wherein the fluid test card includes a bottom shape conforming to the conical shape.

3. The device according to claim 1, further comprising crush ribs disposed on a circumference of said expresser providing an interference fit with an inner circumference of said cylindrical collection vial preventing premature removal of said expresser from said cylindrical collection vial.

4. The device according to claim 3, wherein the support member comprises an outwardly extending flange engaging the vial top.

5. The device according to claim 1, wherein said fluid collector includes a handle and a stem interconnecting said absorbent member and said handle.

6. The device according to claim 5, wherein said fluid collector includes an absorbent member compressing second skirt adjacent said absorbent member, the second skirt being operative upon movement of the inserted fluid collector toward the vial bottom.

7. The device according to claim 6, wherein said absorbent member expands after compression, thereby forcing the skirt against the ring, such expansion preventing fluid drips as the fluid collector and expresser are removed from the vial.

8. The device according to claim 1, wherein said expresser includes a tapered sidewall portion facilitating insertion of said expresser into said cylindrical collection vial.

9. The device according to claim 1, further comprising a cap, which seats the cylindrical collection vial open top.

10. A fluid collection and testing device comprising:
a collection vial having a bottom and an open top, said collection vial comprising a triangular tube;
a fluid test card insertable into said collection vial and including vial bottom wicking fluid test strips;
a expresser, which inserts into the vial open top, said expresser having a ribbed base, which passes fluid therethrough and a support member holding said expresser within said collection vial with said ribbed base in a spaced apart relationship with the collection vial bottom, the collection vial bottom being slanted toward a side of the tube and includes accumulating fluid and fluid test card receiving trough;
a fluid collector including an absorbent member capturing a fluid, said absorbent member being inserted into said expresser and compressible against said ribbed base releasing captured fluid through said ribbed base and into the vial bottom; and a catch mechanism latching said fluid collector to said expresser after insertion of the absorbing member into said expresser and enabling expansion of said absorbent member, after compression, to prevent dripping of fluid upon withdrawal of the fluid collector and expresser from the cylindrical collection vial.

11. A fluid collection and testing device comprising:
a cylindrical collection vial having a bottom and an open top;
an expresser, which inserts into the vial open bottom, said expresser having a ribbed base enabling fluid passing therethrough and a support member holding said expresser within said cylindrical collection vial with said ribbed base in a spaced apart relationship with the vial bottom;
a fluid collector including a fluid capturing absorbent member, said fluid capturing absorbent member being inserted into said expresser and compressible against said ribbed base releasing captured fluid through said ribbed base and into the vial bottom;
a fluid test card, insertable into said cylindrical collection vial and including test strips wicking fluid from the vial bottom, the cylindrical collection vial bottom having an accumulating fluid and fluid test card centering conical shape; and
a catch mechanism latching said fluid collector to said expresser after insertion into said expresser enabling removal of said expresser from said cylindrical collection vial with said fluid collector.

12. The device according to claim 11, wherein the fluid test card includes a bottom conforming to the conical shape.

13. The device according to claim 11, further comprising crush ribs disposed on a circumference of said expresser providing an interference fit with an inner circumference of said cylindrical collection vial preventing premature removal of said expresser from said cylindrical collection vial.

14. The device according to claim 13, wherein support member comprises an outwardly extending flange engaging the vial top.

15. The device according to claim 11, wherein said fluid collector includes a handle and a stem interconnecting said absorbent member and said handle and said catch mechanism includes a skirt radially extending from said stem and a ring disposed on an inner circumference of said cylindrical collection vial engaging said skirt.

16. The device according to claim 15, wherein said fluid collector includes a second skirt adjacent said absorbent member causing compression of said absorbent member against the expresser ribbed base upon movement of the inserted fluid collector toward the vial bottom.

17. The device according to claim 16, wherein said absorbent member expands after compression, thereby forcing the skirt against the ring, such expansion preventing fluid drips as the fluid collector and expresser are removed from the vial.

18. The device according to claim 11, wherein said expresser includes a tapered sidewall portion facilitating insertion of said expresser into said cylindrical collection vial.

19. A fluid collection and testing device comprising:
a collection vial having a bottom and an open top, said collection vial comprises a triangular tube and the vial bottom is slanted toward a side of the tube and includes a trough accumulating fluid and receiving a fluid test card bottom;
an expresser, which inserts into the vial open top, said expresser having a fibbed base, which passes fluid therethrough and a support member holding said expresser within said collection vial with said fibbed base in a spaced apart relationship with the vial bottom;
a fluid collector including an absorbent member capturing a fluid, said absorbent member being inserted into said expresser and compressible against said ribbed base releasing captured fluid through said ribbed base and into the vial bottom; and
a catch mechanism latching said fluid collector to said expresser after insertion into said expresser, which removes said expresser from said collection vial with said fluid collector.

* * * * *